United States Patent
Globerman et al.

(10) Patent No.: US 6,402,777 B1
(45) Date of Patent: Jun. 11, 2002

(54) RADIOPAQUE STENT MARKERS

(75) Inventors: Oren Globerman, Holon; Mordechay Beyar, Caeseria; Rafael Beyar, Haifa, all of (IL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/643,393

(22) Filed: Aug. 22, 2000

Related U.S. Application Data

(63) Continuation of application No. 08/623,739, filed on Apr. 15, 1996.

(30) Foreign Application Priority Data

Mar. 13, 1996 (IL) .................................................. 117472

(51) Int. Cl.$^7$ .................................................. A61F 2/06
(52) U.S. Cl. ..................................... 623/1.11; 623/1.15
(58) Field of Search ............................... 623/1.15, 1.17, 623/1.34, 1.11; 606/191, 198

(56) References Cited

U.S. PATENT DOCUMENTS

| 264,502 A | 9/1882 | Woolson |
|---|---|---|
| 3,902,501 A | 9/1975 | Citron et al. |
| 4,051,592 A | 10/1977 | Briles |
| 4,531,243 A | 7/1985 | Weber et al. |
| 4,733,665 A | 3/1988 | Palmaz |
| 4,828,566 A | 5/1989 | Griss |
| 5,080,674 A | 1/1992 | Jacobs et al. |
| 5,104,404 A | 4/1992 | Wolff |
| 5,306,250 A | 4/1994 | March et al. |
| 5,366,473 A | 11/1994 | Winston et al. |
| 5,443,520 A | 8/1995 | Zweymuller et al. |
| 5,556,413 A | 9/1996 | Lam |
| 5,607,442 A | 3/1997 | Fischell et al. |
| 5,632,771 A | 5/1997 | Boatman et al. |
| 5,725,570 A | 3/1998 | Heath |
| 5,725,572 A | 3/1998 | Lam et al. |
| 5,800,508 A | 9/1998 | Goicoechea et al. |
| 5,824,042 A | 10/1998 | Lombardi et al. |
| 5,824,077 A | 10/1998 | Mayer |
| 6,066,168 A * | 5/2000 | Lau et al. ............... 623/1.16 |
| 6,203,569 B1 * | 3/2001 | Wijay ..................... 623/1.15 |

FOREIGN PATENT DOCUMENTS

| EP | 0 679 372 | 11/1995 |
|---|---|---|
| GB | 1 205 743 A | 9/1970 |
| WO | WO 95/03010 | 2/1995 |

\* cited by examiner

*Primary Examiner*—Michael H. Thaler
(74) *Attorney, Agent, or Firm*—Mueting, Raasch & Gebhardt, P.A.

(57) ABSTRACT

Stents which are inserted into a body lumen preferably are made of materials which are not radiopaque enough, such as S.S. 316L. X-ray visualization of a stent enables an accurate positioning of the stent and also a follow-up of its functioning within the patient's body. The radiopaque markers described here are rivets made of a material which is more radiopaque than the stent substance so the location of the stent can be identified.

19 Claims, 3 Drawing Sheets

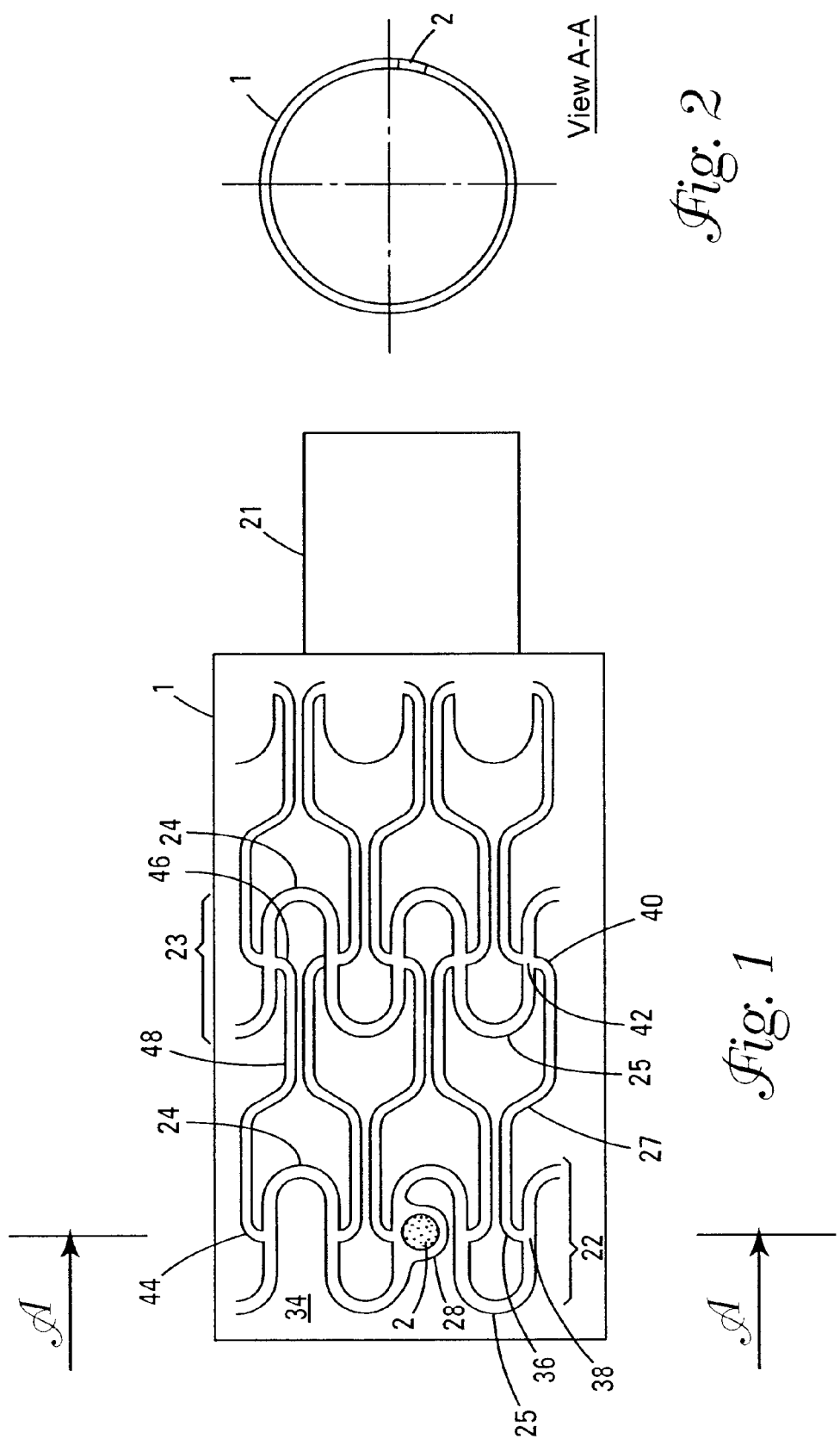

RADIOPAQUE STENT MARKERS

This is a continuation of application Ser. No. 08/632,739, filed Apr. 15, 1996, which is incorporated herein by reference.

FIELD OF THE INVENTION

This invention relates to endoprosthesis devices, generally called stents, and, more particularly, to radiopaque markers for use with endoprosthesis devices.

BACKGROUND OF THE INVENTION

Stents are generally tubular shaped devices that function to hold open a segment of a blood vessel or other anatomical lumen and are useful in the treatment of atherosclerotic stenoses in blood vessels. Stents are particularly suitable for use in supporting and holding back a dissected arterial lining that can occlude the fluid passageway therethrough.

Structures used as stents or intraluminal vascular grafts include coiled stainless steel springs; helical wound spring coil made from shape memory alloy; expanding metal stents formed in a zig-zag pattern; diamond shaped, rectangular shaped, and other mesh and non-mesh designs. Some of the stents currently available employ a self expanding concept, whereby stent expansion is primarily achieved by removing a restraint mechanism holding the stent in a constricted configuration. Other stents in the prior art are delivered to the site by a balloon catheter system, and primarily employ balloon dilation to achieve proper stent expansion.

To accomplish precise placement of stents, various means are employed for identifying the position of the stent within a blood vessel. One means used for accomplishing precise placement of a stent is the attachment to the stent of radiopaque markers so that, through the use of fluoroscopy, the position of the stent within a blood vessel can be identified. Once the stent with its radiopaque markers has been implanted, identification of the stent position during subsequent checkups of the treated segment is easily accomplished because the markers remain visible under fluoroscopy.

In European patent application No. 95302708, assigned to ACS, Inc., a method of coating the stent edges as markers is described. However, this method has several practical disadvantages. First, heavy coating of radiopaque markers onto a stent is somewhat difficult to accomplish. In addition, the radiopaque material might not be attached properly to the stent material and may detach, leaving no way of identifying the position of the stent within the blood vessel. Furthermore, the radiopaque coating may increase the rigidity of the stent, thereby making proper placement difficult and decreasing the stent's effectiveness.

In another method for enabling the precise identification of a stent location using radiopaque markers, commonly assigned U.S. patent application Ser. No. 08/394,799, filed Feb. 27, 1995, discloses a hollow stent having radiopaque material inserted within the hollow stent wire. Because this method of providing radiopaque marking requires that the stent wire is hollow, this method might not be useful where a hollow stent is not desirable.

Another well-known method for enabling the precise identification of a stent location within a blood vessel is producing the stent itself from a radiopaque material such as tantalum. However, a disadvantage of this method is that tantalum is a relatively soft material and it is, therefore, necessary to use more of this metal to achieve sufficient support from the stent.

OBJECTS OF THE INVENTION

It is an object of the invention to provide improved stents.

It is also an object of the invention to provide stents having radiopaque markers.

It is a further object of the invention to provide stents where the distal ends of the stents comprise rivets of material that is more radiopaque than the material from which the stents are made.

These and other objects of the invention will become more apparent in the discussion below.

SUMMARY OF THE INVENTION

The radiopaque markers described below are designed for stents produced from a material that is not sufficiently radiopaque to be seen through the use of fluoroscopy, e.g., a material such as Stainless Steel 316L or nitinol. In order to identify the position of the stent during its insertion into the body and after it has been implanted, however, it is enough to mark the stent edges so that they may be seen under X-ray. The location of the stent will thus be evident based upon the pinpoint locations of its two ends.

According to this invention the edges of the stents are marked by inserting rivets through the ends or edges of the stents, which rivets are made of a material that is more radiopaque than the stent material. For example, if the stent material is S.S. 316L, the rivets can be made of gold, tantalum or platinum.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIG. 1 shows a side elevational view of a portion of a balloon-expandable stent structure having a round opening at each distal end or edge in accordance with an embodiment of this invention;

FIG. 2 shows a cross-sectional view taken along line A—A of FIG. 1 across the entire stent;

DETAILED DESCRIPTION OF THE INVENTION

Figure 3:
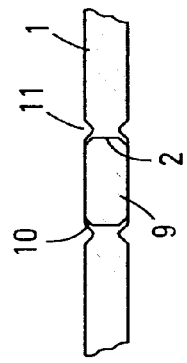
FIG. 3 shows a cross-sectional view of a first embodiment of a rivet inserted through the opening of FIG. 1.

Balloon expandable stent structures are well known in the art. In this invention, as schematically depicted in FIG. 1, a balloon-expandable stent structure 1 deliverable by catheter 21 has an opening 2 at each end of the stent end or edge. In one aspect of the invention, stent structure 1 includes a plurality of radially expandable members that include a first radially expandable member 22 and a second radially expandable member 23, where the first and second radially expandable members 22, 23 are curved into peaks 24 and valleys 25. In one example, the first radially expandable member 22 includes an integral portion that forms a perimeter of the opening 2. FIG. 1 depicts the first radially expandable member 22 forming a first end 34 of the stent 1. In addition, the peaks and valleys of the first radially expandable member 22 are arranged with the peaks and valleys of the second radially expandable member 23 such that the first and second radially expandable members have peaks and valleys that are paired with each other in an in-phase relationship. Interconnecting links 27, each having a curved conformation, extend between first and second radially expandable members 22, 23 such that, for each opening 2, as least one interconnecting link 27 is connected to first radially expandable member 22 at a point on the circumference 28 (perimeter) of the opening 2. In addition, interconnecting links 27, having the curved conformation, are connected by a connection at a first end 36 to a point 38 intermediate a peak and a valley on the first radially expandable member 22 and at a second end 40 to a point 42 intermediate a peak and a valley on the radially second expandable member 23. The interconnecting links 27 illustrated in FIG. 1 have at least one bend 44 adjacent to the connecting point 38 on the first radially expandable member 22 and at least one bend 46 adjacent the connecting point 38 on the second radially expandable member 23 and at least one straight section 48 there between. In a first embodiment of the invention, the opening 2 are round. FIG. 2 shows a cross-section of the stent 1 and shows opening 2 passing radially from the external stent surface into the internal stent surface.

According to the invention a marker having radiopaque qualities is inserted through the opening at each end or edge of the stent to mark the ends of the stent so that the position of the stent can be determined by the location of its ends when the markers are seen under X-ray. Because the markers are placed securely into and through holes or openings, they are referred to as "rivets".

FIG. 3 illustrates the placement of a rivet 3 into a stent opening 2. Rivet 3 comprises a short rod made from a radiopaque material, which is compressed into the opening 2 in the axial direction 4, thereby compressing the radiopaque material and causing a circumferential force 5 that enables rivet 3 to be held within opening 2 of stent 6. Because retention of the marker rivet requires an opening whose aperture size does not vary while the rivet is inserted therein, the preferred location of the marker rivet is a region of the stent that is not deformed during expansion of the stent. In particular, for a balloon-expandable stent, this will usually be at an edge of the stent, at the end of the stent's lattice-like structure.

Figure 4:
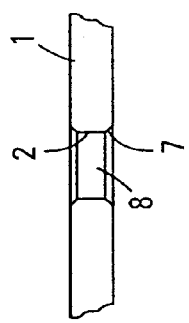
FIG. 4 shows a cross-sectional view of a second embodiment of a rivet inserted through the opening of FIG. 1.

As shown in FIG. 4, an alternative manner of assuring that the rivet remains in the stent opening 2 is to form the rivet edges 7 with a cone-like, outwardly radiating shape, i.e., with beveled edges. Then, after the radiopaque rivet 8 is compressed into opening 2, the rivet 3 cannot leave the stent due to the friction between the edges 7 of the rivet and the outer edges of the inner walls of opening 2.

Figure 5:
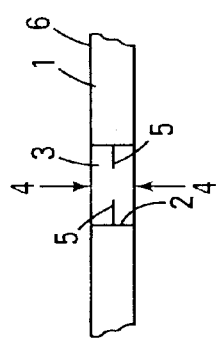
FIG. 5 shows a cross-sectional view of a third embodiment of a rivet inserted through the opening of FIG. 1.

Another means of securing the rivet within the lumen is shown in FIG. 5, in which the marker rivet 9 is made with chamfered edges 10. After rivet 9 is inserted into the opening 2, the stent 1 is pressed at points 11 so the marker rivet 9 cannot displace from the stent.

Figure 6:
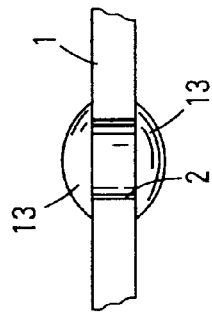
FIG. 6 shows a cross-sectional view of a fourth embodiment of a rivet inserted through the opening of FIG. 1.
Figure 7:
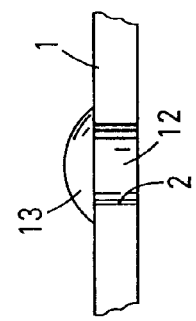
FIG. 7 shows a cross-sectional view of a fifth embodiment of a rivet inserted through the opening of FIG.

In a further embodiment of the invention illustrated in FIG. 6, an enlarged head portion 13 of rivet 12 protrudes from opening 2 on one side of the stent in a diameter larger than that of the rivet portion situated within opening 2. Thus, when the stent is viewed through X-ray, a larger height and greater diameter of the rivets and, therefore, a better visualization of the markers of the ends of the stent, is achieved. FIG. 7 illustrates a variation of this embodiment of the rivet in which the enlarged head portion 13 protrudes from both sides of the stent, achieving even larger height and greater diameter of the rivet and still better visualization of the rivet, and thus the stent ends, under X-ray.

Figure 8:
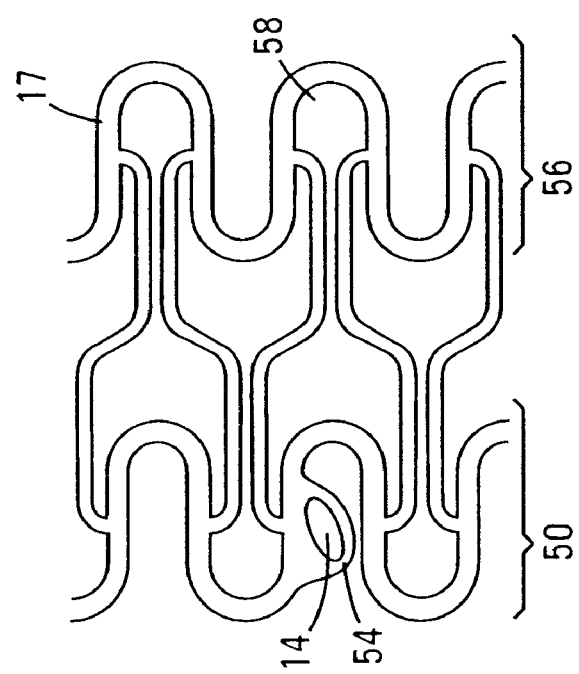
FIG. 8 shows a side elevational view of a portion of a balloon-expandable stent structure having a second embodiment of an opening at each edge.

FIG. 8 illustrates a second embodiment of the invention. FIG. 8 includes a first radially expandable member 50 with an integral portion that forms a perimeter 54 of opening 14. The opening 14 of the stent 17 is non-round, such as oval. The non-round opening 14 allows a non-round rivet to be inserted therein. This serves to enlarge the rivet surface without interfering with the fluid flow within the stent. FIG. 8 further includes a second radially expandable member 56 at a second end 58 of the stent 17. The second radially expandable member 56 can include an integral portion that forms a perimeter of at least one opening. A third radially expandable member can be included intermediate the first and second radially expandable members, where the stent can further include an integral portion of the radially expandable member that forms a perimeter of at least one opening. In one embodiment, the openings formed in the first and second radially expandable members are aligned with at least one opening formed in the third radially expandable member. The openings can also be located in a region of the stent that is not deformed during radial expansion of the stent.

Figure 9:
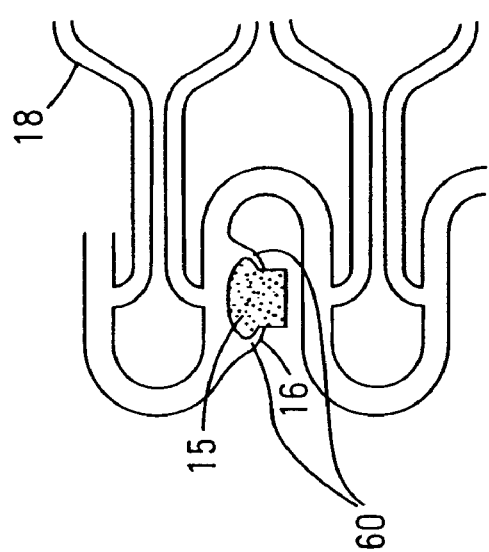
FIG. 9 shows a side elevational view of a portion of a balloon expandable stent structure having a third embodiment of an opening and showing a marker inserted through the opening.

In the embodiment of this invention illustrated in FIG. 1 through FIG. 8, marker rivets are completely surrounded by the stent material (e.g., perimeter) so that they either are contained within the stent material or project only from the external and internal surfaces of the stent. Another embodiment of the invention and an additional type of marker rivet is shown in FIG. 9, in which the integral portion of the stent 18 where the marker is placed is not a loop or an opening passing radially through the stent material 18 but is rather a circumferential space defined by a perimeter 60 that includes two circumferential detent projections 16. The corresponding marker 15 is pressed circumferentially into the space defined by the perimeter 60 and is held there by specially designed projections 16 into adequate shape in the marker. This method enables an insertion of a marker with larger visible surface area by allowing the larger surface area to fit along and be co-extensive with the stent circumference as opposed to projecting radially into and out of the stent shape.

The above-described markers are designed for both stent extremities in order to define the ends of the stent during fluoroscopy. Nonetheless these markers can be combined onto the entire stent length and also on several places located along the stent circumference, so that the stent diameter can be detected during fluoroscopy, as well. It is within the scope of the invention that a stent could have, for example, from 2 to 20 marker rivets, located from about 0.5 to 5 cm apart longitudinally and/or from 1 to 4 rivets spaced radially, preferably equidistantly, or a combination thereof.

As described above, the rivets are preferably compressed into the stent material. Optionally, in addition to or in place of compression, the surface between the rivets and the stent can be heated to weld or fuse the rivets into position. Preferably such heating would be focused heating, for example, with a laser, where only the rivet and stent material would be present.

This invention is intended primarily for use with balloon-expandable stents, although it is envisioned that the technology disclosed herein is applicable to other medical devices, including, but not limited to, self-expanding stents. An important factor is that the material of the rivet be more radiopaque than the primary material used in the device. For example, if a balloon-expandable stent is comprised of stainless steel or nitinol, then rivets comprised of gold, platinum, or titanium would be useful.

The invention herein is not limited to a particular latticework for a balloon-expandable stent. However, the invention is especially useful with the balloon-expandable stents described in co-pending U.S. patent application Ser. No. 08/543,337, filed Oct. 16, 1995, now U.S. Pat. No. 5,776,161 incorporated herein by reference.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

We claim:

1. A medical device comprising:
    a catheter and a stent mounted on the catheter, the stent comprising:
        first and second radially expandable members, each of said first and second radially expandable members curved into peaks and valleys;
        at least one opening integrally formed in the first radially expandable member such that the opening occupies at least a portion of the area defined by a peak or valley;
        radiopaque marker material forming a rivet in each opening; and
        a plurality of interconnecting links each having a curved conformation, the interconnecting links extending between the first and second radially expandable members such that, for each opening, at least one interconnecting link is connected to the first radially expandable member at a point on the circumference of the opening.

2. A medical device as in claim 1 wherein the peaks and valleys of the first radially expandable member are arranged with the peaks and valleys of the second radially expandable member such that the first and second radially expandable members have peaks and valleys which are paired with each other in an in-phase relationship.

3. A medical device as in claim 1 wherein each of the plurality of interconnecting links is connected at a first end to a point intermediate a peak and a valley on the first radially expandable member and at a second end to a point intermediate a peak and a valley on the radially second expandable member.

4. A medical device as in claim 3 wherein the plurality of interconnecting links are connected to said first and second radially expandable members such that each intermediate point between a peak and a valley includes a connection to one of the interconnecting links.

5. A medical device as in claim 1 wherein each of the plurality of interconnecting links has at least one bend adjacent to a connecting point on the first radially expandable member and at least one bend adjacent a connecting point on the second radially expandable member and at least one straight section therebetween.

6. A medical device as in claim 1 wherein the edges of the opening are either beveled or are chamfered toward the center of the opening.

7. A medical device as in claim 1 wherein the outer surface of the rivet is flush with the outer surface of the stent.

8. A medical device as in claim 1 wherein the opening is located in a region of the stent that is not deformed during radial expansion of the stent.

9. A medical device as in claim 1 wherein first radially expandable member comprises between one and four openings containing the radiopaque marker material.

10. A medical device as in claim 1 comprising between 2 and 20 openings containing the radiopaque marker material.

11. A medical device comprising:
    a catheter and a stent mounted on the catheter, the stent comprising:
        a plurality of radially expandable members comprising a first radially expandable member comprising a first distal end of said stent, each of said radially expandable members curved into peaks and valleys;
        at least one opening integrally formed in the first radially expandable member such that the opening occupies at least a portion of the area defined by a peak or valley;
        radiopaque marker material forming a rivet in each opening; and
        a plurality of interconnecting links each having a curved conformation, the interconnecting links extending between adjacent radially expandable members, such that, for each opening, at least one interconnecting link is connected to the first radially expandable member at a point on the circumference of the opening.

12. A medical device as in claim 11 wherein the plurality of radially expandable members further comprises a second radially expandable member comprising a second distal end of stent, the stent further comprising at least one opening integrally formed in the second radially expandable member such that the opening occupies at least a portion of the area defined by a peak or a valley.

13. A medical device as is claim 12 wherein the plurality of radially expandable members further comprises a third radially expandable member intermediate the first and second radially expandable members, the stent further comprising at least one opening integrally formed in a third radially expandable member such that the opening occupies at least a portion of the area defined by a peak or valley.

14. A medical device as in claim 13 wherein the openings formed in the first and second radially expandable members are longitudinally aligned with at least one opening formed in the third radially expandable member.

15. A medical device as in claim 11 wherein the edges of the opening are either beveled or are chamfered toward the center of the opening.

16. A medical device as in claim 11 wherein the outer surface of the rivet is flush with the outer surface of the stent.

17. A medical device as in claim 11 wherein the opening is located in a region of the stent that is not deformed during radial expansion of the stent.

18. A medical device as in claim 11 wherein first radially expandable member comprises between one and four openings containing the radiopaque marker material.

19. A medical device as in claim 11 comprising between 2 and 20 openings containing the radiopaque marker material.

* * * * *

UNITED STATES PATENT AND TRADEMARK OFFICE
CERTIFICATE OF CORRECTION

PATENT NO. : 6,402,777 B1
DATED : June 11, 2002
INVENTOR(S) : Globerman et al.

It is certified that error appears in the above-identified patent and that said Letters Patent is hereby corrected as shown below:

Title page
Item [63], Related U.S. Application Data, please delete "Continuation of application No. 08/623,739", and insert -- Continuation of application No. 08/632,739 --;
Item [56], References Cited, U.S. PATENT DOCUMENTS, after 6,066,168, please delete "A" and insert -- B1 --;

Column 5,
Line 29, please delete "at least one opening integrally formed in the first radially expandable member such that the opening occupies at least a portion of the area defined by a peak or valley;", and replace with -- an integral portion of said first radially expandable member forming a perimeter of at least one opening; --;
Line 33, after "a rivet in each", please insert -- said at least one --;
Line 38, after "members such that, for each", please insert -- said at least one --;
Line 39, please delete "one interconnecting link is connected to the first radially expandable member at a point on the circumference of the opening.", and replace with -- one interconnecting link is connected to said first radially expandable member at a point on said perimeter of said at least one opening. --;

Column 6,
Lines 16-17, after "comprising a first", please delete "distal";
Line 19, please delete "at least one opening integrally formed in the first radially expandable member such that the opening occupies at least a portion of the area defined by a peak or valley;" and replace with -- an integral portion of said first radially expandable member forming a perimeter of at least one opening; --;
Line 23, after "forming a rivet in each", please insert -- said at least one --;
Line 28, delete "for each opening, at least one interconnecting link is connected to the first radially expandable member at a point on the circumference of the opening.", and replace with -- for each said at least one opening, at least one interconnecting link is connected to said first radially expandable member at a point on said perimeter of said at least one opening. --;
Line 35, after "second", delete "distal";
Line 36, after "of", insert -- the --;
Line 36, after "further comprising", insert -- an integral portion of said second radially expandable member forming a perimeter of --;

UNITED STATES PATENT AND TRADEMARK OFFICE
CERTIFICATE OF CORRECTION

PATENT NO.    : 6,402,777 B1
DATED         : June 11, 2002
INVENTOR(S)   : Globerman et al.

It is certified that error appears in the above-identified patent and that said Letters Patent is hereby corrected as shown below:

Column 6 (cont'd),
Lines 36-37, after "at least one opening", please delete "integrally formed in the second radially expandable member such that the opening occupies at least a portion of the area defined by a peak or a valley";
Lines 43-44, after "the stent further comprising", please insert -- an integral portion of said third radially expandable member forming a perimeter of --;
Line 44, after "at least one opening", please delete "integrally formed in a third radially expandable member such that the opening occupies at least a portion of the area defined by a peak or valley";

Signed and Sealed this

Tenth Day of December, 2002

JAMES E. ROGAN
*Director of the United States Patent and Trademark Office*